United States Patent
Wei et al.

(10) Patent No.: US 7,613,506 B2
(45) Date of Patent: Nov. 3, 2009

(54) METHOD FOR DERIVING STANDARD 12-LEAD ELECTROCARDIOGRAM, AND MONITORING APPARATUS USING THE SAME

(75) Inventors: Daming Wei, The University of Aizu Faculty House A307, 17-26, Matsunaga 1-chome, Ikki-machi, Aizuwakamatsu-shi, Fukushima (JP); Yoshio Sakai, Tokyo (JP)

(73) Assignees: Nihon Kohden Corporation, Tokyo (JP); Daming Wei, Fukushima (JP)

( * ) Notice: Subject to any disclaimer, the term of this patent is extended or adjusted under 35 U.S.C. 154(b) by 563 days.

(21) Appl. No.: 11/212,565

(22) Filed: Aug. 29, 2005

(65) Prior Publication Data

US 2006/0047212 A1  Mar. 2, 2006

(30) Foreign Application Priority Data

Aug. 27, 2004 (JP) ............................ P2004-248016

(51) Int. Cl.
*A61B 5/04* (2006.01)
(52) U.S. Cl. ...................................... 600/509; 600/512
(58) Field of Classification Search ................. 600/509, 600/513, 512, 514, 515, 516
See application file for complete search history.

(56) References Cited

U.S. PATENT DOCUMENTS 5,711,304 A * 1/1998 Dower ......................... 600/523
2002/0045837 A1 * 4/2002 Wei et al. ..................... 600/509
2002/0072777 A1 * 6/2002 Lu ................................ 607/17
2003/0167013 A1 * 9/2003 Anatoly et al. ............... 600/509
2004/0088017 A1 * 5/2004 Sharma et al. ................ 607/25
2006/0235317 A1 * 10/2006 Wei .............................. 600/509
2006/0247700 A1 * 11/2006 Jackson ......................... 607/9

FOREIGN PATENT DOCUMENTS

JP  2002-34943 A  2/2002
JP  2002-282229 A  10/2002

* cited by examiner

*Primary Examiner*—Carl H. Layno
*Assistant Examiner*—Jon-Eric C. Morales
(74) *Attorney, Agent, or Firm*—Sughrue Mion, PLLC

(57) ABSTRACT

Four first electrodes are attached on right clavicle, the vicinity of on left clavicle, on right lowermost rib, and the position on left lowermost rib, corresponding to limb leads 12-lead electrocardiogram (ECG). Two second electrodes are attached on such positions of the living body that correspond to a lead V2 and a lead V4 of 12-lead ECG. First ECG data set correspond to leads I and II of 12-lead ECG. A second ECG data set including the leads V2 and V4. A heart vector is calculated on the first and second ECG data sets, and predetermined first lead vectors of leads I, II, V2 and V4. A third ECG data set including leads V1, V3, V5 and V6 is calculated based on the heart vector and predetermined second lead vectors of leads V1, V3, V5 and V6. A fourth ECG data set from leads III, aVR, aVL and aVF of 12-lead ECG based on the first ECG data set. The 12-lead ECG is derived based on the first to fourth ECG data sets.

4 Claims, 3 Drawing Sheets

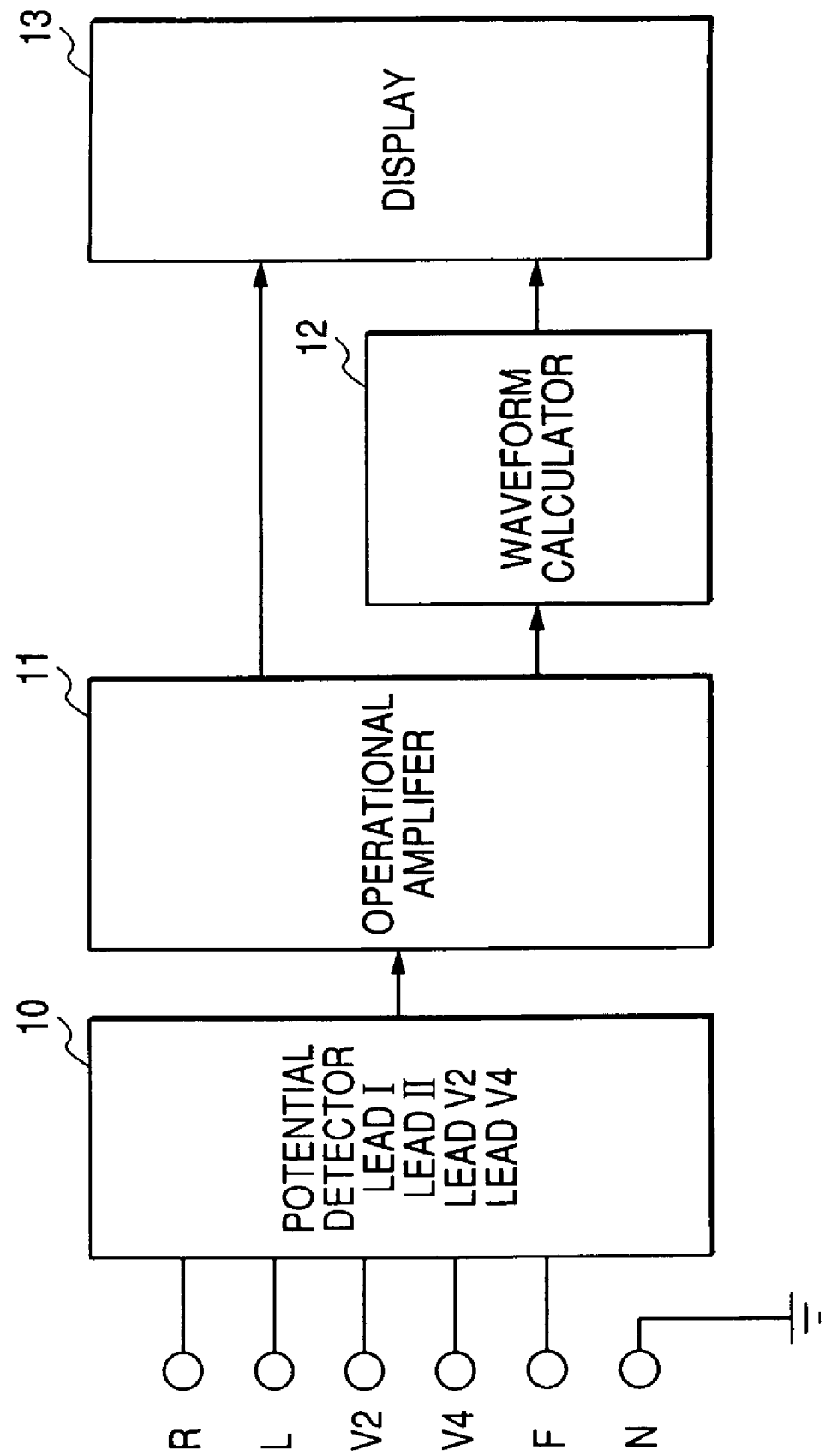

METHOD FOR DERIVING STANDARD 12-LEAD ELECTROCARDIOGRAM, AND MONITORING APPARATUS USING THE SAME

BACKGROUND OF THE INVENTION

The present invention relates to a method for deriving a standard 12-lead electrocardiogram effective for diagnosing ischemic heart disease, acute myocardial infarction, or the like, in which a minimum number of electrodes are attached to predetermined areas on the body surface of a living body. The present invention also relates to a monitoring apparatus using such a method.

Conventionally, when an electrocardiogram of a patient is detected, measured, and recorded in a hospital or a like facility, a total of ten electrodes are attached to the body surface of the patient; namely, six positions for chest leads, and four positions for limb leads. Six limb-lead waveforms (I, II, III, aVR, aVL, and aVF) of standard 12-lead waveforms and six chest-lead waveforms (V1, V2, V3, V4, V5, and V6) of the same are derived from electric potentials of the heart detected and measured by the ten electrodes by measuring means, such as an electrocardiograph.

The related-art electrocardiograph or the like can detect, measure, and record an electrocardiogram which is formed from standard 12-lead waveforms and allows appropriate diagnosis and treatment of a variety of heart diseases, through use of ten electrodes. Such a diagnosis and treatment using a plurality of electrodes is possible in a fully-equipped hospital, or the like, where a patient is maintained at rest. However, when at-home or emergency medical treatment is to be performed, no time is available for attaching a large number of electrodes to appropriate positions on the body surface of the living body, from the viewpoint of the status of the patient; moreover, difficulty is encountered in transmitting a large number of lead waveforms in the form of multi-channel signals. In addition, since only one channel (i.e., one lead) or a like number of channels of an electrocardiogram signal can be generally radio-transmitted, a heart disease is diagnosed with an electrocardiogram through use of a few number of electrodes (two to four electrodes).

Furthermore, the following configuration has been conventionally practiced as means for detecting and recording an electrocardiogram of standard 12-lead waveforms with a small number of electrodes. For example, four special positions (four electrodes of EASI) on the chest surface of a living body are used, and respective electrocardiographic waveforms thereof are lead. Once signals of the electrocardiographic waveforms have been converted into a vectorcardiogram with use of a fixed coefficient, the thus-converted vectorcardiogram is converted into a 12-lead electrocardiogram. The thus-obtained electrocardiogram is known as an EASI-lead electrocardiogram.

In the lead method of the EASI-lead electrocardiogram of the related art, an approximation to a standard 12-lead electrocardiogram can be attained to a certain degree. However, when leads from the four special positions on the chest surface of the living body are emplaced, appropriate attachment of the electrodes to respective specified positions encounters difficulty, since health care professionals, such as doctors and nurses, are not clinically accustomed to this attachment work, thereby posing a problem of variation arising in detection accuracy of the electrocardiogram. In addition, as described above, when arithmetic operation is performed to acquire the 12-lead electrocardiogram from the electrocardiographic signals derived from the electrodes, the signals must be converted twice (from EASI leads to a vectorcardiogram, and from the vectorcardiogram to a 12-lead electrocardiogram) through use of the fixed coefficient. Accordingly, in some cases variation arises in calculation accuracy. Furthermore, since none of the leads are actually measured values of the 12 leads, some doubts arise with regard to reliability.

General relationships among lead waveforms and measurement positions shown in FIGS. 4A and 4B, and potentials for obtaining a 12-lead electrocardiogram are as follows,

TABLE 1

| | |
|---|---|
| I | vL − vR |
| II | vF − vR |
| III | vF − vL |
| aVR | vR − (vL + vF)/2 |
| aVL | vL − (vR + vF)/2 |
| aVF | vF − (vL + vR)/2 |
| V1 | v1 − (vR + vL + vF)/3 |
| V2 | v2 − (vR + vL + vF)/3 |
| V3 | v3 − (vR + vL + vF)/3 |
| V4 | v4 − (vR + vL + vF)/3 |
| V5 | v5 − (vR + vL + vF)/3 |
| V6 | v6 − (vR + vL + vF)/3 |

Accordingly, in the lead method for the EASI lead electrocardiogram of the related art, positions to which the EASI electrodes are attached for measuring respective potentials are special and differ from those of the measurement positions of the lead waveforms of the case shown in Table 1. Therefore, accuracy in positioning to the specified positions in attachment of the electrodes poses considerable influences to a measurement result which is inconvenient, in that the attachment requires rich experience, and the like. In addition, even when a patent is resting in a fully equipped hospital, or the like, the number of the electrodes used for the standard 12-lead measurement is large. Accordingly, problems arise not only in terms of inconvenience for the patient, but also in terms of increased load on a health care professional who applies the electrodes.

From the above viewpoints, Japanese Patent Publication No. 2002-34943A proposes a method and an electrocardiograph for deriving a standard 12-lead electrocardiogram which enables appropriate diagnosis and treatment of a variety of heart diseases by making use of a lead system subset constituted of the minimum number of leads for obtaining a conventionally-known standard 12-lead electrocardiogram or an M-L leads (Mason-Likar leads) electrocardiogram; and filed a patent application therefor.

Specifically, this method utilizes, as a lead system subset Constituted of the minimum number of channels, for instance, leads I and II of limb leads in standard 12-lead system or ML leads, and leads V1, and V5 or V6 of chest leads which have been used for obtaining the standard 12-lead electrocardiogram. By virtue of the configuration, lead III and leads aVR, aVL, and aVF are calculated on the basis of intrinsic relationships among the leads shown in Table 1. The remaining chest leads V2, V3, V4, and V6 or V5 are calculated on the basis of relationships between the potential matrix, the lead vectors and the heart vectors.

In the case of limb leads, electrodes for deriving lead waveforms I and II are disposed at four positions constituted of the left and right arms (LA and RA), and left and right legs (LL and RL). In the case of ML leads, the electrodes are disposed at four positions constituted of parts below the left and right clavicles (LA and RA), and lower ends of the left and right anterior iliac spines or the left and right coastal arches (LL and RL). In this case, RL is caused to serve as a grounding electrode.

In addition, electrodes for deriving lead waveforms from two leads (V1, and V6 or V5) of chest leads are disposed at two positions constituted of the right margin of sternum in the fourth intercostal (V1), and a position on the left middle axillary line at the level of the fifth intercostal left midclavicular line (V6) or a position on the left anterior axillary line at the level of the fifth intercostal left midclavicular line (V5).

The lead system subset of the standard 12-lead electrocardiogram can be detected and measured; and the remaining leads of the standard 12-lead electrocardiogram can be calculated on the basis of the intrinsic relationships among the respective leads shown in Table 1.

A standard 12-lead electrocardiogram obtained as above utilizes the lead system subset of the related-art standard 12-lead electrocardiogram. Therefore, in attachment of the electrodes, positioning to the respective specified positions can be performed easily and without fail without requiring rich experience for the work. Hence, a highly-accurate standard 12-lead electrocardiogram can be derived, thereby enabling appropriate diagnosis and treatment of a variety of heart diseases.

As described above, when the patient complains of a symptom, such as chest pain or chest tightness, which is suspected to indicate angina pectoris or myocardial infarction, at the emergency treatment, an emergency medical staff, cardiovascular doctor, or the like, determines whether or not a 12-lead electrocardiogram includes an ischemic variation of the ST segment. If necessary, the patient is immediately transported to a cardiovascular-specialized hospital well-equipped with a CCU, and the like, which evidently leads to an increase in a survival rate of the patient.

Accordingly, desire has arisen for deriving a 12-lead electrocardiogram which is equivalent to a standard 12-lead electrocardiogram, in which leads of the well-known standard 12-lead electrocardiogram are simplified to the greatest possible extent, which has an accuracy sufficient to determine occurrence of angina pectoris and myocardial infarction, which is derived from a minimum number of electrodes, and, furthermore, in which attachment of the electrodes is facilitated.

On the other hand, under the method for deriving a standard 12-lead electrocardiogram disclosed in Japanese Patent Publication No. 2002-34943A, an instantaneous electromotive force vector (a heart vector) is obtained by making use of a subset of a lead system of a standard 12-lead electrocardiogram, and electrocardiographic potentials of unknown leads are calculated from the heart vector. According to this deriving method, limb lead electrodes are attached to positions of the ML-leads for use in an exercise stress testing electrocardiogram in place of two wrists and two ankles. More specifically, these electrode positions are located inward of the arm roots so as to be unaffected by arm movements during exercise, and are offset from an electrical lead line connecting the two arms and the heart. This offset can result in an error of lead vectors for calculation of an electrocardiogram derived from unknown leads.

In addition, as combinations of electrodes for deriving chest leads, leads V1 and V5 or leads V1 and V6 are selected. However, since electrical angles formed with these leads are close to 180 degrees, when an electrical angle formed with a heart vector and one of the pair of selected leads closes to the right angle, an electrical angle formed with the heart vector and the other one of the selected leads also closes to the right angle. In such a situation, since the lead potential closes to zero, probability of an error in calculation of the heart vector may be increased.

SUMMARY OF THE INVENTION

It is therefore an object of the invention to provide a method and a monitoring apparatus for deriving a standard 12-lead electrocardiogram which enables derivation of a standard 12-lead electrocardiogram easily, conveniently and accurately through the use of a minimum number of electrodes; and which is capable of easily and effectively attaining monitoring for appropriate diagnosis and treatment of a variety of heart diseases.

In order to achieve the above object, according to the invention, there is provided a method of deriving a standard 12-lead electrocardiogram, comprising:

attaching four first electrodes on the vicinity of a lower right end of a right clavicle, the vicinity of a lower left end of a left clavicle, the vicinity of a position on a right anterior axillary line at the level of a right lowermost rib, and the vicinity of a position on a left anterior axillary line at the level of a left lowermost rib of a living body, so as to correspond to limb leads of the standard 12-lead electrocardiogram;

attaching two second electrodes on such positions of the living body that correspond to a lead V2 and a lead V4 of chest leads of the standard 12-lead electrocardiogram;

measuring a first electrocardiogram data set corresponding to a lead I and a lead II of the standard 12-lead electrocardiogram with the first electrodes;

measuring a second electrocardiogram data set including the lead V2 and the lead V4 with the second electrodes;

calculating an instantaneous electromotive force cardiac vector (a heart vector) based on the first electrocardiogram data set, the second electrocardiogram data set, and predetermined first lead vectors of the lead I, the lead II, the lead V2 and the lead V4;

calculating a third electrocardiogram data set Including a lead V1, a lead V3, a lead V5 and a lead V6 of the chest leads based on the heart vector and predetermined second lead vectors of the lead V1, the lead V3, the lead V5 and the lead V6;

calculating a fourth electrocardiogram data set corresponding to a lead III, a lead aVR, a lead aVL and a lead aVF of the standard 12-lead electrocardiogram based on the first electrocardiogram data set; and deriving the standard 12-lead electrocardiogram based on the first electrocardiogram data set, the second electrocardiogram data set, the third electrocardiogram data set and the fourth electrocardiogram data set.

With the above configuration, the positions of the first electrodes can be identified very easily. In addition, since the respective electrodes are located on an electrical lead line connecting two wrists and the heart, it is possible to reduce an error between the results obtained by the invention and the original limb leads of the standard 12-lead electrocardiogram.

In addition, since the position of the lead V2 is located at the fourth intercostal left sternal border, and that of the lead V4 is located at an intersecting point of the fifth intercostal and the mid-clavicle line, the positions for the second electrodes are positions that can be most easily identified among the chest leads. Furthermore, a space for attaching a pad for applying defibrillation on the patient suffering ventricular fibrillation can be ensured. Moreover, since an overall reduction is achieved in a sum of electrical angles formed with a direction of the heart vector and the lead vectors of unknown leads V1, V3, V5, and V6, in addition to the leads I and II measured from the limb leads, an error can be minimized.

As illustrated in FIG. 4, the leads V2 and V4 form angles closest to the normal electric angle (the angle of an average electromotive force of the heart). Therefore, the above use of chest leads is the best way to calculate a heart vector.

Preferably, each of the first lead vectors is predetermined as an independent vector having a direction component which is made identical with direction components of the other lead vectors and a magnitude component which is optimized in accordance with electrical angles with respect to the lead V1, the lead V3, the lead V5 and the lead V6.

In a case where lead vectors of unknown leads V1, V3, V5, and V6 for use in obtaining a heart vector are determined on the basis of a position of the heart and electrode positions of a model of an average build, magnitude of those lead vectors; that is, sensitivity at a time when an instantaneous electromotive force of the heart is transmitted through a living body and appears on a surface of the body can be defined in an optimized manner on the basis of electrical angles formed with lead vectors of unknown leads and lead vectors of leads I, II, V2, and V4 for use in calculation of the third electrocardiogram data set. Accordingly, an error in synthesis of an electrocardiogram due to the build of the patient, attachment positions of electrodes, or positional offset of the heart resulting from body position change can be minimized.

According to the invention, there is also provided a monitoring apparatus for deriving a standard 12-lead electrocardiogram, comprising:

four first electrodes, adapted to be attached on the vicinity of a lower right end of a right clavicle, the vicinity of a lower left end of a left clavicle, the vicinity of a position on a right anterior axillary line at the level of a right lowermost rib, and the vicinity of a position on a left anterior axillary line at the level of a left lowermost rib of a living body, so as to correspond to limb leads of the standard 12-lead electrocardiogram;

two second electrodes, adapted to be attached on such positions of the living body that correspond to a lead V2 and a lead V4 of chest leads of the standard 12-lead electrocardiogram;

a first detector, operable to measure a first electrocardiogram data set corresponding to a lead I and a lead II of the standard 12-lead electrocardiogram with the first electrodes;

a second detector, operable to measure a second electrocardiogram data set including the lead V2 and the lead V4 with the second electrodes;

a first calculator, operable to calculate an instantaneous electromotive force vector (a heart vector) based on the first electrocardiogram data set, the second electrocardiogram data set, and predetermined first lead vectors of the lead I, the lead II, the lead V2 and the lead V4;

a second calculator, operable to calculate a third electrocardiogram data set including a lead V1, a lead V3, a lead V5 and a lead V6 of the chest leads based on the heart vector and predetermined second lead vectors of the lead V1, the lead V3, the lead V5 and the lead V6;

a third calculator, operable to calculate a fourth electrocardiogram data set corresponding to a lead III, a lead aVR, a lead aVL and a lead aVF of the standard 12-lead electrocardiogram based on the first electrocardiogram data set; and a display, operable to display the standard 12-lead electrocardiogram based on the first electrocardiogram data set, the second electrocardiogram data set, the third electrocardiogram data set and the fourth electrocardiogram data set.

With this configuration, highly-accurate electrocardiogram data corresponding to the standard 12-lead electrocardiogram set can be obtained easily with attachment of a minimum number of electrodes without requiring rich experience, thereby easily and effectively attaining monitoring for conducting appropriate diagnosis and treatment of a variety of heart diseases.

BRIEF DESCRIPTION OF THE DRAWINGS

The above objects and advantages of the present invention will become more apparent by describing in detail preferred exemplary embodiments thereof with reference to the accompanying drawings, wherein:

FIG. 6 is a block diagram of a monitoring apparatus according to one embodiment of the invention.

DETAILED DESCRIPTION OF THE EMBODIMENTS

Embodiments of the present invention will be described below in detail with reference to the accompanying drawings.

Figure 5:
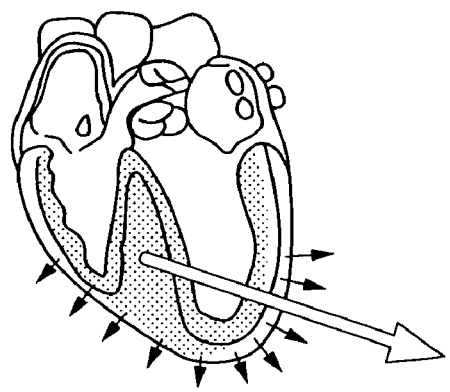
FIG. 5 is a diagram showing a heart vector obtained by synthesizing electromotive forces generated in heat muscles.

A rationale for deriving a 12-lead electrocardiogram according to the invention is as follows. In a clinical electrocardiogram a standard 12-lead electrocardiogram is derived by detecting potentials on the basis of Table 1 in accordance with a lead theory. According to the theory, as shown in FIG. 5, an instantaneous electromotive force of the heart at an arbitrary time can be expressed by dipoles at fixed positions; and a potential (V) at an arbitrary lead position can be calculated from the following equation.

$$V = L \cdot H \tag{1}$$

where V denotes a potential matrix, H denotes a heart vector, and L denotes a lead vector.

The lead vector L of a person was measured by Frank as early as 1953 with use of an artificial human-body model, and this measurement has been recognized to be effective as a foundation of the current vector electrocardiogram. In addition, since the heart vector H is a spatial vector whose position is fixed, the heart vector H has only three independent parameters. Accordingly, parameters of the heart vector H can be calculated from three or more leads having such spatial information. Once the heart vector H is obtained, potentials of the remainder of the 12 leads can also be calculated by making use of the heart vector H and the lead vector L.

For instance, the following relationships can be set as a method for measuring two leads (I and II) of limb leads and two leads (V2 and V4) of chest leads, to thus obtain a heart vector H, thereby calculating potentials of the remaining leads (V1, V3, VS, and V6) of the chest leads.

$$V1 = L1 \cdot H$$

$$V3 = L3 \cdot H$$

$$V5 = L5 \cdot H$$

$$V6 = L6 \cdot H \tag{2}$$

The above Equations (2) are derived from the Equation (1) while being extended in a general form as V=LH. In the case of Equation (2), $$V = \begin{bmatrix} V1 \\ V3 \\ V5 \\ V6 \end{bmatrix}$$

$$L = \begin{bmatrix} L1^T \\ L3^T \\ L5^T \\ L6^T \end{bmatrix} \text{ where,}$$

$$Li = \begin{bmatrix} l_x \\ l_y \\ l_z \end{bmatrix} \quad i = 1, 3, 5 \text{ and } 6, \text{ and}$$

$$H = \begin{bmatrix} h_x \\ h_y \\ h_z \end{bmatrix}$$

Here, T denotes transposition operation of a vector or a matrix. By applying measured potentials from lead I, II, V2 and V4, the heart vector H can be calculated from the following Equation (3).

$$H = (L^T L)^{-1} \cdot L^T \cdot V \quad \text{where} \tag{3}$$

$$L = \begin{bmatrix} LI^T \\ LII^T \\ L2^T \\ L4^T \end{bmatrix} \text{ and}$$

$$V = \begin{bmatrix} VI \\ VII \\ V2 \\ V4 \end{bmatrix}$$

Figure 1:
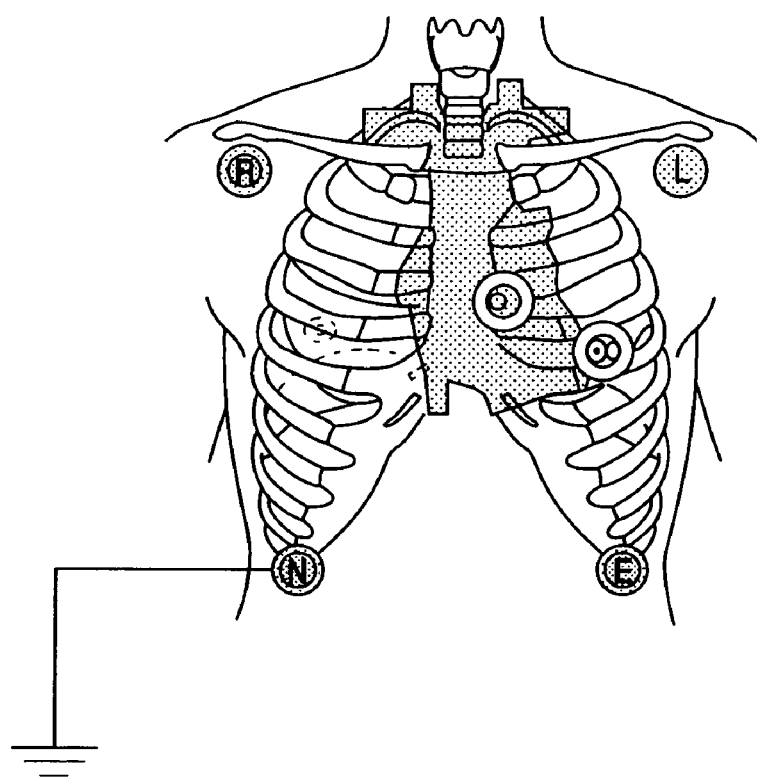
FIG. 1 is a diagram showing positions of electrodes according to a method for deriving a standard 12-lead electrocardiogram of the invention.

Next, a method of deriving a 12-lead electrocardiogram in accordance with the above-mentioned basic principles of the invention will be described FIG. 1 shows an example arrangement of electrodes to be attached on the surface of a living body for deriving electrocardiographic waveform data as an electrocardiogram data set with use of a monitoring apparatus for a derived 12-lead electrocardiogram of the embodiment. In the embodiment, electrodes are respectively disposed at positions R, L, F, N, C2, and C4 in the drawing.

In this case, in FIG. 1, R, L, F, and N are positions for deriving leads corresponding to limb leads of a standard 12-lead electrocardiogram; and are set such that positions for electrodes which are originally placed at the right wrist, left wrist, right ankle, and left ankle for deriving the standard 12-lead electrocardiogram are respectively placed in the vicinity of the lower right end of the right clavicle, the vicinity of the lower left end of the left clavicle, the vicinity of a position on the right anterior axillary line at the level of the right lowermost rib, and the vicinity of a position on-the left anterior axillary line at the level of the left lowermost rib. Meanwhile, N is employed as a grounding electrode.

These electrode positions R, L, F, and N, which are originally placed at wrists and ankles for deriving the limb leads of the standard 12-lead electrocardiogram, are placed in the chest and located on an electrical line connecting the two wrists and ankles via the heart. In such positions, the attachment of electrodes is facilitated. Hence, there can be derived electrocardiographic waveform data serving as an electrocardiogram data set equivalent to I, II, III, aVR, aVL, and aVF which are derived by electrodes set in accordance with limb leads of a standard 12-lead electrocardiogram.

In addition, in FIG. 1, C2 and C4 denote the same electrode positions as those of the leads V2 and V4 of chest leads of a standard 12-lead electrocardiogram. Accordingly, when electrodes are attached to the electrode positions C2 and C4, electrocardiographic waveform data serving as an electrocardiogram data set corresponding to the leads V2 and V4 of the standard 12-lead electrocardiogram can be derived.

As described above, with use of the electrocardiographic waveform data (I, II, V2, and V4) equivalent to or corresponding to a standard 12-lead electrocardiogram derived by the electrodes attached to the respective electrode positions R, L, F, N, C2, and C4, the previously-mentioned heart vector H is obtained; and on the basis of Equation (2), potentials corresponding to the remaining chest leads (V1, V3, V5, and V6) of the standard 12-lead electrocardiogram are calculated, thereby deriving a 12-lead electrocardiogram of the invention.

In addition, in Equation (3), the heart vector H can be obtained on the basis of lead vectors of the leads I, II, V2, and V4, and potentials measured by the electrodes of the leads I, II, V2, and V4. Subsequently, electrocardiographic waveforms of respective unknown leads (V1, V3, V5, and V6) are calculated with use of Equation (2). At this time, with a view toward minimizing errors resulting from synthesis of an electrocardiogram including builds of the patient attachment positions of electrodes, positional offset of the heart resulting from body position change, and individual differences in lead vectors, magnitudes of the lead vectors of the leads I, II, V2, and V4 are optimized (L1, L3, L5, and L6) in consideration of electrical angles formed with the lead vectors of unknown leads (V1, V3, V5, and V6) to be calculated and lead vectors of the leads I, II, V2, and V4, thereby obtaining heart vectors corresponding to the respective unknown leads. Subsequently, the respective electrocardiographic waveforms are calculated from an average value of heart vectors.

Figure 2:
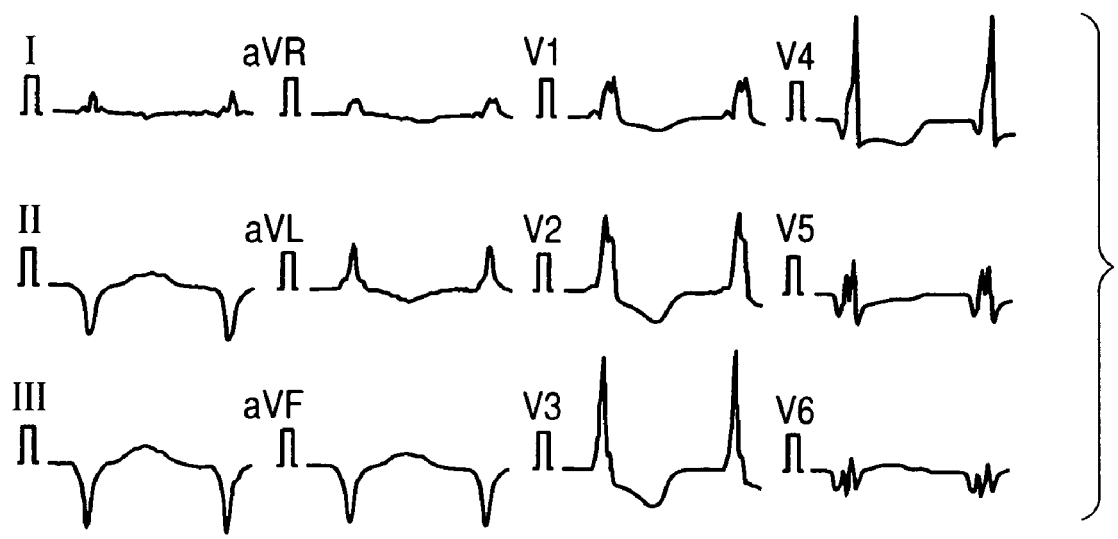
FIG. 2 shows waveforms measured by 10 electrodes placed at positions defined by the standard 12-lead electrocardiogram.
Figure 3:
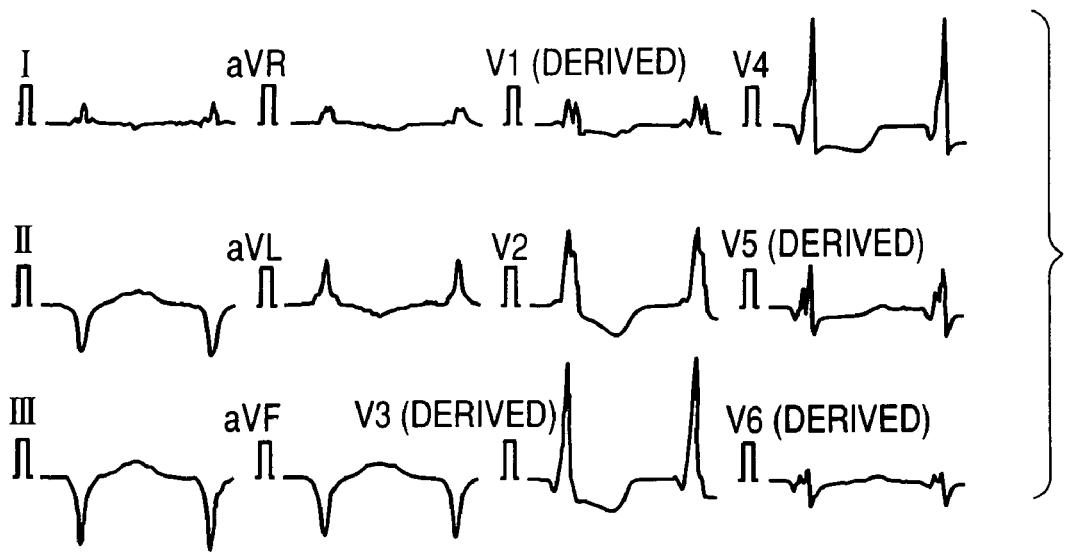
FIG. 3 shows waveform derived by the method of the invention.
Figure 4:
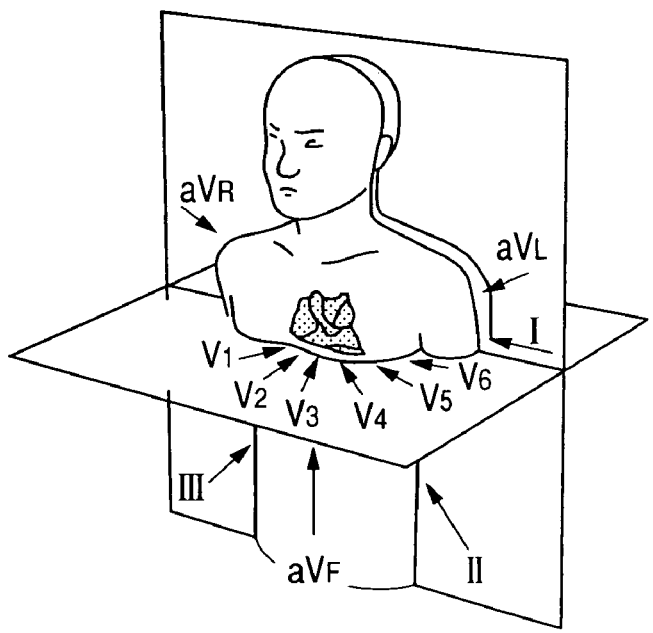
FIG. 4 is a diagram for explaining anatomical position relationships between limb leads and chest leads of the standard 12-lead electrocardiogram.

FIG. 2 shows respective electrocardiographic waveforms of a case where standard 12-lead electrocardiographic waveforms (I, II, III, aVR, aVL, aVF, V1 V2, V3, V4, V5, and V6) of a resting patient suffering myocardial infarction are measured, Potentials of the leads I, II, V2, and V4 are measured in accordance with the above-described configuration, and potentials of the remaining chest leads (V1, V3, V5, and V6) are calculated with the arithmetic equations. FIG. 3 shows the result. Thus, comparison between the actual measured values of the standard 12-lead electrocardiogram shown in FIG. 2 and the derived 12-lead electrocardiogram including leads (V1, V3, V5, and V6) synthesized in accordance with calculations shown in FIG. 3 indicates that occurrence of suspected myocardial infarction can be confirmed in both diagrams.

FIG. 6 is a view showing a system configuration of a monitoring apparatus which uses the method for deriving a 12-lead electrocardiogram described above. More specifically, a potential detector 10 is configured such that potentials of two leads (I and II) corresponding to limb leads of a standard 12-lead electrocardiogram and two leads (V2 and V4) of chest leads are respectively derived by electrodes (R, L, F, N, C2, and C4) disposed on a body surface of a living body shown In FIG. 1. In addition, an operational amplifier 11 is configured so as to calculate and amplify electrocardiographic waveform data on the basis of potentials detected and measured by the potential detector 10, thereby inputting into a waveform calculator 12; as well as combining synthesized electrocardiographic waveform data output from the waveform calculator 12 and the electrocardiographic waveform data output from the operation amplifier 11, thereby deriving a 12-lead electrocardiogram, and displaying the derived 12-lead electrocardiogram on a display 13.

Accordingly, the monitoring apparatus of the above configuration is capable of attaining appropriate and effective monitoring of a derived 12-lead electrocardiogram corresponding a standard 12-lead electrocardiogram when measurement of the standard 12-lead electrocardiogram is difficult in such cases as at a bedside in an ICU, CCU, and the like in a hospital, or a like facility; during home care; during emergency treatment; and during an exercise stress testing.

Although the present invention has been shown and described with reference to specific preferred embodiments, various changes and modifications will be apparent to those skilled in the art from the teachings herein. Such changes and modifications as are obvious are deemed to come within the spirit, scope and contemplation of the invention as defined in the appended claims.

What is claimed is:

1. A method of deriving a standard 12-lead electrocardiogram, comprising:

attaching four first electrodes on the vicinity of a lower right end of a right clavicle, the vicinity of a lower left end of a left clavicle, the vicinity of a position on a right anterior axillary line at the level of a right lowermost rib, and the vicinity of a position on a left anterior axillary line at the level of a left lowermost rib of a living body, so as to correspond to limb leads of the standard 12-lead electrocardiogram;

attaching two second electrodes on such positions of the living body that correspond to a lead V2 and a lead V4 of chest leads of the standard 12-lead electrocardiogram;

measuring a first electrocardiogram data set corresponding to a lead I and a lead II of the standard 12-lead electrocardiogram with the first electrodes;

measuring a second electrocardiogram data set including the lead V2 and the lead V4 with the second electrodes;

calculating an instantaneous electromotive force vector (a heart vector) based on the first electrocardiogram data set, the second electrocardiogram data set, and predetermined first lead vectors of the lead I, the lead II, the lead V2 and the lead V4;

calculating a third electrocardiogram data set including a lead V1, a lead V3, a lead V5 and a lead V6 of the chest leads based on the heart vector and predetermined second lead vectors of the lead V1, the lead V3, the lead V5 and the lead V6;

calculating a fourth electrocardiogram data set corresponding to a lead III, a lead aVR, a lead aVL and a lead aVF of the standard 12-lead electrocardiogram based on the first electrocardiogram data set; and deriving the standard 12-lead electrocardiogram based on the first electrocardiogram data set, the second electrocardiogram data set, the third electrocardiogram data set and the fourth electrocardiogram data set.

2. The derivation method as set forth in claim 1, wherein each of the first lead vectors is predetermined as an independent vector having a direction component which is made identical with direction components of the other lead vectors and a magnitude component which is optimized in accordance with electrical angles with respect to the lead V1, the lead V3, the lead V5 and the lead V6.

3. A monitoring apparatus for deriving a standard 12-lead electrocardiogram, comprising:

four first electrodes, adapted to be attached to positions of the living body in the vicinity of a lower right end of a right clavicle, the vicinity of a lower left end of a left clavicle, the vicinity of a position on a right anterior axillary line at the level of a right lowermost rib, and the vicinity of a position on a left anterior axillary line at the level of a left lowermost rib of a living body, so as to correspond to limb leads of the standard 12-lead electrocardiogram;

two second electrodes, adapted to be attached to positions of the living body that correspond to a lead V2 and a lead V4 of chest leads of the standard 12-lead electrocardiogram;

a first detector, operable to measure a first electrocardiogram data set corresponding to a lead I and a lead II of the standard 12-lead electrocardiogram with the first electrodes;

a second detector, operable to measure a second electrocardiogram data set including the lead V2 and the lead V4 with the second electrodes;

a first calculator, operable to calculate an instantaneous electromotive force vector (a heart vector) based on the first electrocardiogram data set, the second electrocardiogram data set, and predetermined first lead vectors of the lead I, the lead II, the lead V2 and the lead V4;

a second calculator, operable to calculate a third electrocardiogram data set including a lead V1, a lead V3, a lead V5 and a lead V6 of the chest leads based on the heart cardiac vector and predetermined second lead vectors of the lead V1, the lead V3, the lead V5 and the lead V6;

a third calculator, operable to calculate a fourth electrocardiogram data set corresponding to a lead III, a lead aVR, a lead aVL and a lead aVF of the standard 12-lead electrocardiogram based on the first electrocardiogram data set; and a display, operable to display the standard 12-lead electrocardiogram based on the first electrocardiogram data set, the second electrocardiogram data set, the third electrocardiogram data set and the fourth electrocardiogram data set.

4. The monitoring apparatus as set forth in claim 3, wherein each of the first lead vectors is predetermined as an independent vector having a direction component which is made identical with direction components of the other lead vectors and a magnitude component which is optimized in accordance with electrical angles with respect to the lead V1, the lead V3, the lead V5 and the lead V6.

* * * * *